(12) United States Patent
Pei et al.

(10) Patent No.: US 10,791,996 B2
(45) Date of Patent: Oct. 6, 2020

(54) INTRAOPERATIVE NERVE EVALUATION DEVICE AND SYSTEM, AND METHOD FOR PERFORMING INTRAOPERATIVE NERVE EVALUATION

(71) Applicants: Chang Gung University, Taoyuan (TW); Chang Gung Memorial Hospital, Linkou, Taoyuan (TW)

(72) Inventors: Yu-Cheng Pei, Taoyuan (TW); Ting-Yu Chen, Taoyuan (TW); Cheng-Hung Lin, Taoyuan (TW); Jian-Jia Huang, Taoyuan (TW)

(73) Assignees: Chang Gung University, Taoyuan (TW); Chang Gung Memorial Hospital, Linkou, Taoyuan (TW)

( * ) Notice: Subject to any disclaimer, the term of this patent is extended or adjusted under 35 U.S.C. 154(b) by 453 days.

(21) Appl. No.: 15/817,348

(22) Filed: Nov. 20, 2017

(65) Prior Publication Data
US 2018/0199894 A1    Jul. 19, 2018

(30) Foreign Application Priority Data
Jan. 17, 2017  (TW) .............................. 106101476 A

(51) Int. Cl.
*A61B 5/00* (2006.01)
*A61B 5/04* (2006.01)
*A61N 1/372* (2006.01)
*A61B 5/0488* (2006.01)
(Continued)

(52) U.S. Cl.
CPC ........ *A61B 5/7282* (2013.01); *A61B 5/04001* (2013.01); *A61B 5/4041* (2013.01); *A61B 5/7217* (2013.01); *A61B 5/7278* (2013.01); *A61B 5/742* (2013.01); *A61B 5/0488* (2013.01); *A61B 5/7225* (2013.01); *A61B 2562/0209* (2013.01); *A61B 2562/164* (2013.01); *A61N 1/0551* (2013.01); *A61N 1/36034* (2017.08); *A61N 1/3727* (2013.01)

(58) Field of Classification Search
None
See application file for complete search history.

(56) References Cited

U.S. PATENT DOCUMENTS

2010/0145222 A1\* 6/2010 Brunnett ............ A61B 5/04001
                                                              600/554
2012/0130459 A1\* 5/2012 Kim ................... A61B 5/04001
                                                              607/115
(Continued)

*Primary Examiner* — Jacqueline Cheng
*Assistant Examiner* — Jairo H Portillo
(74) *Attorney, Agent, or Firm* — Peter A. Nieves; Sheehan Phinney Bass & Green PA

(57) ABSTRACT

An intraoperative nerve evaluation device includes a flexible substrate, and a plurality of detection units disposed on the substrate and spaced apart from one another. Each of the detection units includes an electrode and a conductive wire electrically connected to the electrode. When the electrodes are attached to a nerve, a selected one of the electrodes is configured to receive an input signal via the corresponding conductive wire and to transmit the input signal to the nerve, and each of the electrodes other than the selected one is configured to receive from the nerve a response signal associated with the input signal and to transmit the response signal via the corresponding conductive wire.

11 Claims, 10 Drawing Sheets

(51) Int. Cl.
*A61N 1/05* (2006.01)
*A61N 1/36* (2006.01)

(56) References Cited

U.S. PATENT DOCUMENTS

2014/0100639 A1* 4/2014 Lee .................. A61L 31/16
607/116
2016/0235329 A1* 8/2016 Bernstein ................ A61B 8/48

* cited by examiner

INTRAOPERATIVE NERVE EVALUATION DEVICE AND SYSTEM, AND METHOD FOR PERFORMING INTRAOPERATIVE NERVE EVALUATION

CROSS-REFERENCE TO RELATED APPLICATION

This application claims priority of Taiwanese Patent Application No. 106101476, filed on Jan. 17, 2017.

FIELD

The disclosure relates to intraoperative neuromonitoring device and system, and a method for performing intraoperative nerve evaluation.

BACKGROUND

Conventionally, a number of ways may be employed to monitor functional integrity of a nerve so as to evaluate whether a nerve is injured during surgery. For example, the nerve may be inspected visually by a surgeon. Alternatively, a biopsy operation may be implemented for the evaluation of the nerve. A conventional nerve evaluation device may also be employed for performing in vitro and/or in vivo evaluation. However, visual inspection is inaccurate, and the biopsy operation is not only time-consuming but also unable to provide evaluation result in real time. As for the conventional nerve evaluation device, it has to be moved frequently to locate the injured part of the nerve.

SUMMARY

One object of the disclosure is to provide an intraoperative nerve evaluation device.

According to one embodiment of the disclosure, the intraoperative neuromonitoring device includes a flexible substrate and a plurality of detection units.

The detection units are disposed on the substrate, and are spaced apart from one another. Each of the detection units includes an electrode configured to be attached to a nerve of a subject, and a conductive wire electrically connected to the electrode.

When the electrodes of the detection units are attached to the nerve, the electrode of a selected one of the detection units is configured to receive an input signal via the conductive wire of the selected one of the detection units and to transmit the input signal to the nerve, and the electrode of each of the detection units other than the selected one is configured to receive, from the nerve, a response signal associated with the input signal and to transmit the response signal via the conductive wire of the detection unit.

Another object of the disclosure is to provide an intraoperative nerve assessment system that includes the aforementioned intraoperative neuromonitoring device, and is capable of analyzing the signals so as to determine whether the nerve is injured.

According to one embodiment of the disclosure, the intraoperative nerve assessment system includes an intraoperative nerve assessment device, a controller, a signal input module, a signal amplifier module, and a display.

The intraoperative nerve assessment device includes a flexible substrate, and multi-channel detection units. The detection units are disposed on the substrate and spaced apart from one another. Each of the detection units includes an electrode and a conductive wire electrically connected to the electrode. The electrodes of the detection units are configured to be attached a nerve.

The signal input module is electrically connected to the conductive wire of a selected one of the detection units, and is configured to transmit the input signal to the electrode of the selected one of the detection units. The controller is electrically connected to the signal input module, and is configured to control operation of the signal input module.

The signal amplifier module is electrically connected to the controller and the conductive wires of the detection units other than the selected one, and is configured to receive, from the conductive wires connected thereto, a number of response signals associated with the input signal, to amplify the response signals, and to transmit amplified response signals to the controller.

The display is coupled to the controller and is controlled by the controller to display the amplified response signals.

Yet another object of the disclosure is to provide a method for performing intraoperative nerve evaluation, to be implemented by the abovementioned system.

The method includes steps of, when the electrodes of the detection units are attached to respective parts of a nerve of a subject, the signal input module is electrically connected to the conductive wire of a selected one of the detection units, and the signal amplifier module is electrically connected to the conductive wire of each of the detection units other than the selected one:

a) controlling, by the controller, the signal input module to transmit an input signal to the electrode of the selected one of the detection units via the conductive wire of the selected one of the detection units;

b) receiving, by the signal amplifier module, a number of response signals from the conductive wires of the detection units other than the selected one;

c) amplifying, by the signal amplifier module, the number of response signals;

d) receiving, by the controller, a number of amplifying response signals from the signal amplifier module; and e) controlling, by the controller, the display to display the number of amplifying response signals.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
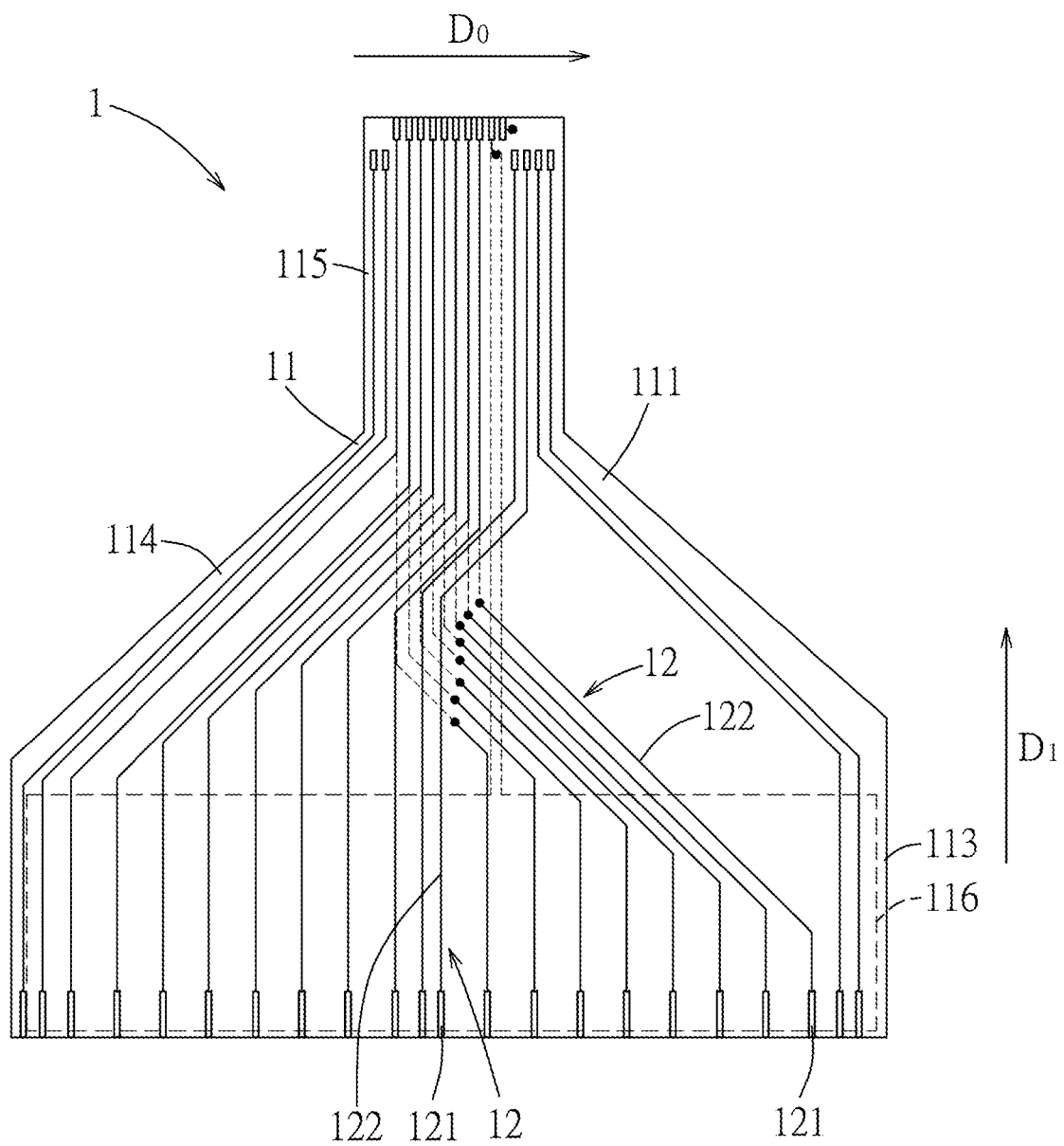
FIG. 1 is a schematic view of a first surface of an intraoperative nerve evaluation device according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

FIG. 1 illustrates an intraoperative nerve evaluation device 1 according to one embodiment of the disclosure. The intraoperative nerve evaluation device 1 includes a flexible substrate 11 and a plurality of detection units 12.

In this embodiment, the substrate 11 is made of polyimide (PI), and may take the form of a plate. The detection units 12 are disposed on the substrate 11, and are spaced apart from one another.

Each of the detection units 12 includes an electrode 121, and a conductive wire 122 electrically connected to the electrode 121 for transmitting signals. The electrodes 121 of the detection units 12 are aligned in a row in a first direction ($D_0$).

Figure 2:
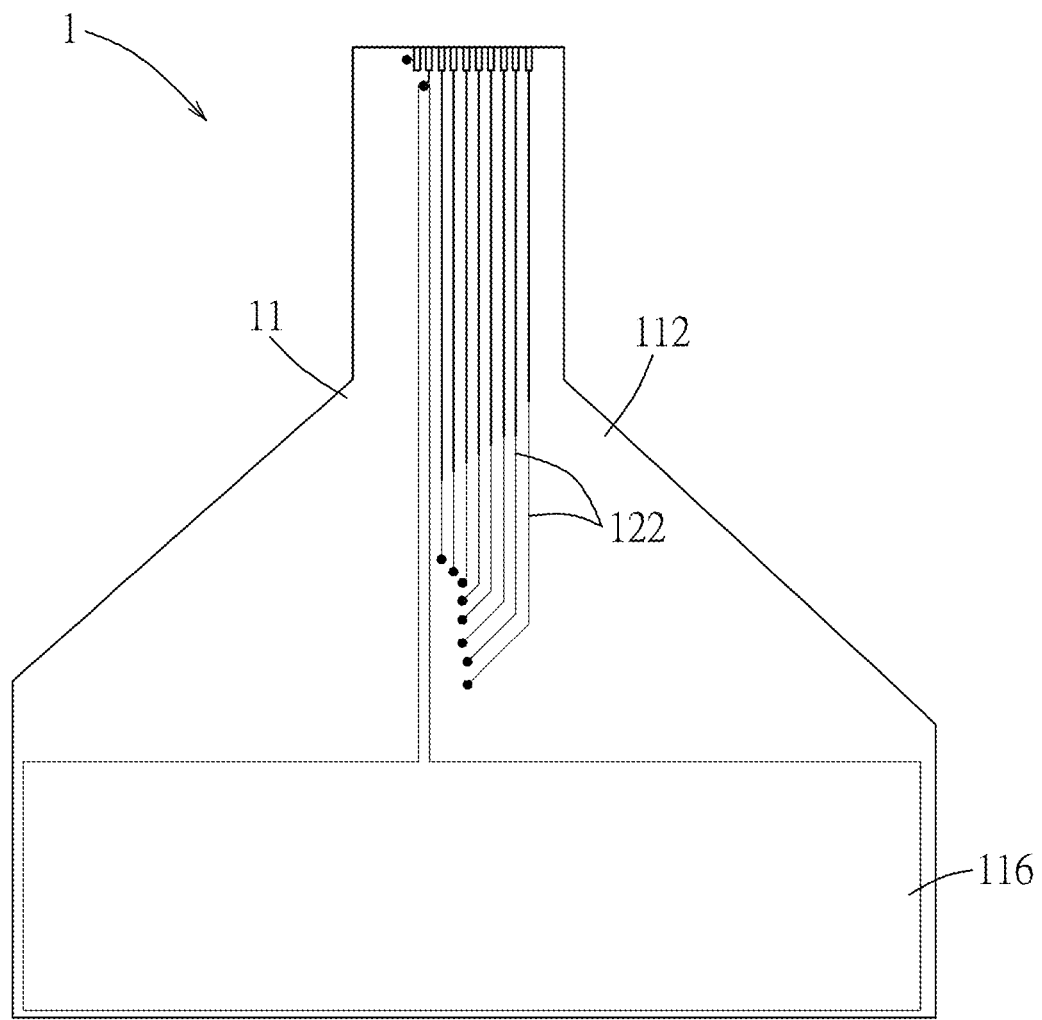
FIG. 2 is a schematic view of a second surface of the intraoperative nerve evaluation device according to one embodiment of the disclosure.

Further referring to FIG. 2, the substrate 11 has a first surface 111, and a second surface 112 that is opposite to the first surface 111. Additionally, a number of parts may be defined for the substrate 11. For example, in this embodiment the substrate 11 has an electrode part 113, a wire part 114 and an extension part 115.

The wire part 114 extends and substantially tapers from the electrode part 113 in a second direction ($D_1$) perpendicular to the first direction ($D_0$). That is to say, a width of the wire part 114 gradually decreases in the second direction ($D_1$) from the electrode part 113. The extension part 115 extends from one side of the wire part 114 opposite to the electrode part 113 in the second direction ($D_1$). Namely, a width of the extension part 115 in the first direction ($D_0$) is smaller than that of the electrode part 113; and the wire part 114 is disposed between the electrode part 113 and the extension part 115, and the width thereof gradually decreases in the direction ($D_1$) from the electrode part 113 to the extension part 115.

The electrodes 121 of the detection units 12 are disposed on the electrode part 113. The conductive wire 122 of each detection unit 12 extends from the electrode part 113 through the wire part 114 to the extension part 115.

The arrangement of the conductive wires 122 may be made such that areas of the first surface 111 and the second surface 112 may be smaller. For example, in this embodiment, some of the conductive wires 122 are entirely arranged on the first surface 111, and others of the conductive wires 122 are each arranged to first extend on the first surface 111, pass through the substrate 11, and then extend to the extension part 115 on the second surface 112 (see FIG. 2).

In such a configuration, since some of the conductive wires 122 are arranged partly on the second surface 112 when extending to the extension part 115, the width of the extension part 115 may be made smaller than that of the electrode part 113, and therefore the cost for manufacturing the intraoperative nerve evaluation device 1 may be reduced.

The intraoperative nerve evaluation device 1 may further include a conductive metal layer 116 disposed on the second surface 112 for the purpose of grounding.

Figure 3:
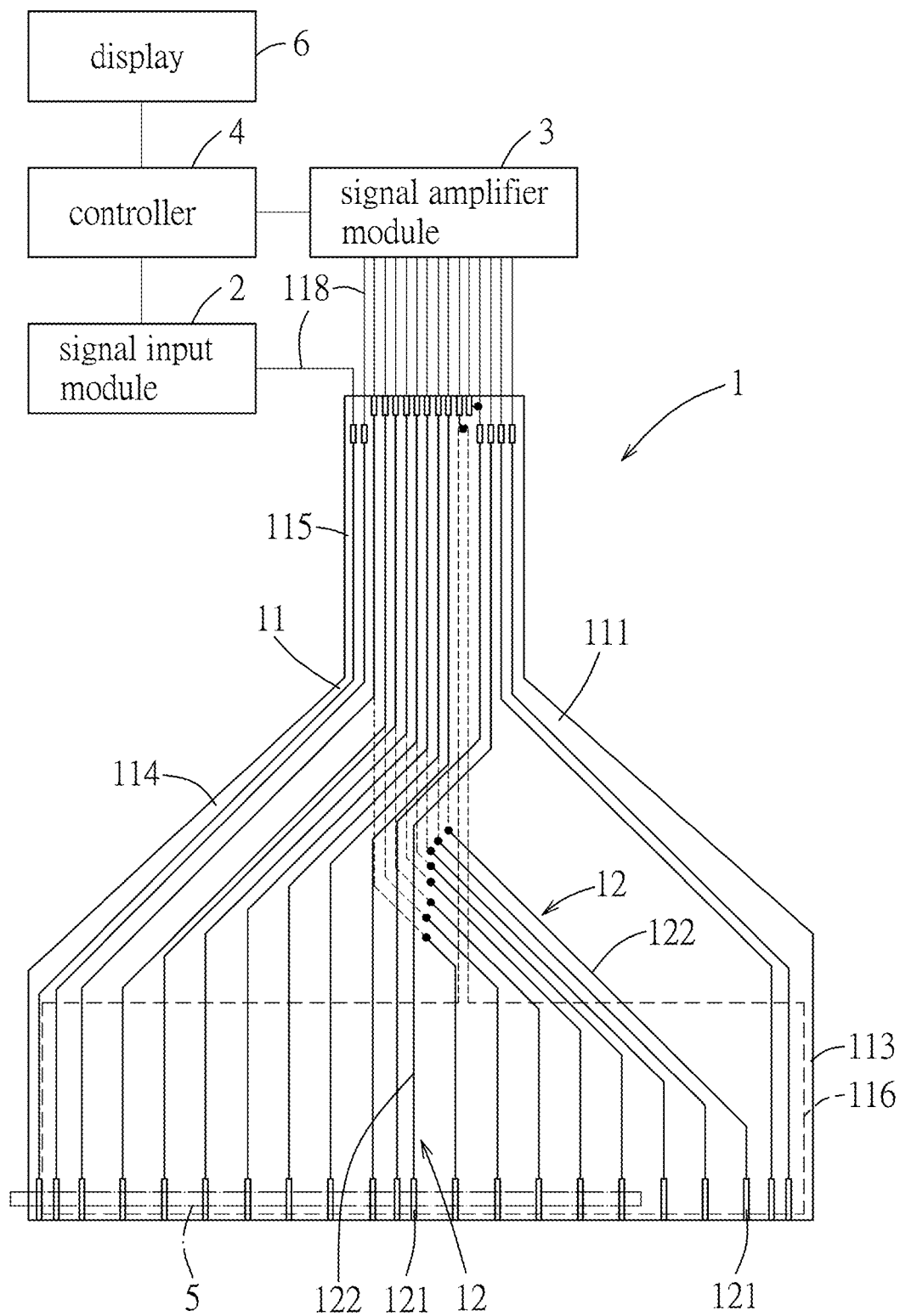
FIG. 3 is a schematic view of an intraoperative nerve evaluation system attached to a nerve, according to one embodiment of the disclosure.

FIG. 3 illustrates an intraoperative nerve evaluation system that includes the intraoperative nerve evaluation device 1 as illustrated in FIGS. 1 and 2, according to one embodiment of the disclosure.

In this embodiment, the intraoperative nerve evaluation system further includes a signal input module 2, a signal amplifier module 3, a controller 4 and a display 6.

In use, the intraoperative nerve evaluation system is for monitoring a nerve 5 of a subject.

The signal input module 2 is electrically connected to the controller 4 and the conductive wire 122 of a selected one of the detection units 12.

The signal amplifier module 3 is electrically connected to the controller 4 and the conductive wires 122 of the detection units 12 other than the selected one of the detection units 12.

It is noted that, the signal input module 2 and the signal amplifier module 3 may be embodied using a signal generator and an electronic amplifier, respectively, or using circuitry blocks. The electrical connections from the signal input module 2 and the signal amplifier module 3 to the conductive wires 122 may be done using a number of bus lines 118.

In use, the electrodes 121 are attached to the nerve 5. The controller 4 is capable of controlling the signal input module 2 to transmit an input signal to the electrode 121 of the selected one of the detection units 12.

In response to the input signal, reactions of the nerve 5 may be picked up by the electrodes 121 of the detection units 12 other than the selected one of the detection units 12 in the form of response signals. The response signals are transmitted through the corresponding conductive wires 122, and then are received by the signal amplifier module 3, which is programmed to amplify the response signals and to transmit the amplified response signals to the controller 4. The display 6 is coupled to the controller 4 and is controlled by the controller 4 to display the response signals amplified by the signal amplifier module 3.

Figure 4:
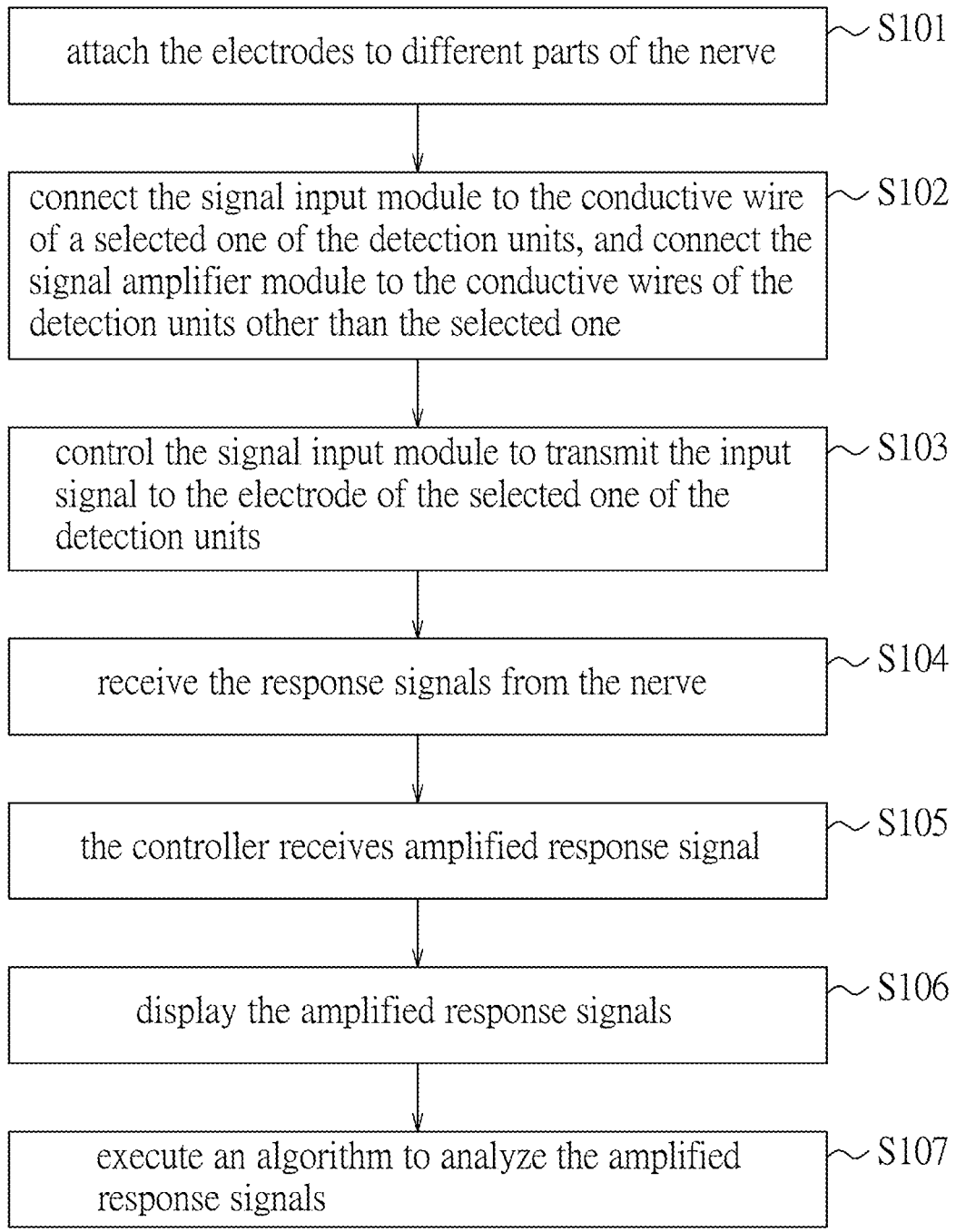
FIG. 4 illustrates an operation during which a method for performing intraoperative nerve evaluation is implemented, according to one embodiment of the disclosure.

FIG. 4 illustrates an operation during which a method for performing intraoperative nerve evaluation is implemented by the intraoperative nerve evaluation system shown in FIG. 3.

Before implementation of the method, in step S101 of the operation, the electrodes 121 are attached to different parts of the nerve 5. This step may be performed by a person, such as a medical personnel. It is noted that, since the substrate 11 is made flexible, the electrodes 121 may be more fittingly attached to the nerve 5, which may come in various shapes. Additionally, the electrode part 113 may be bent along the first direction ($D_0$), such that the operation of placing the electrodes 121 in vivo may be rendered more convenient. In step S102, the signal input module 2 is electrically connected to the conductive wire 122 of the selected one of the detection units 12, and the signal amplifier module 3 is electrically connected to the conductive wires 122 of the detection units 12 other than the selected one. Similarly, the electrical connection among the signal input module 2, the amplifier module 3 and the conductive wires 122 may be done by the medical personnel.

Afterwards, in step S103, the controller 4 controls the signal input module 2 to transmit the input signal to the electrode 121 of the selected one of the detection units 12 via the corresponding conductive wire 122.

Figure 5:
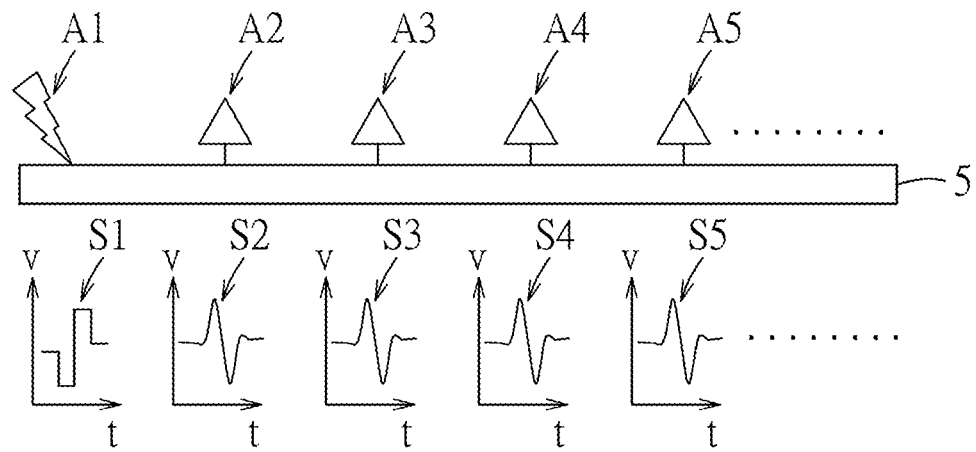
FIG. 5 illustrates an input signal being applied to one end of a healthy nerve and response signals resulting from the input signal.

In one example illustrated in FIGS. 3 and 5, a leftmost one of the detection units 12, corresponding with a frontmost end of the nerve 5, is selected. Accordingly, the corresponding conductive wire 122 is electrically connected to the input module 2.

Specifically, as shown in FIG. 5, the input signal (A1) having a waveform (S1) is applied to the nerve 5. In this embodiment, the input signal (A1) is a bipolar stimulation signal.

Then, in step S104, the response signals from the nerve 5 are detected by the electrodes 121 of the detection units 12 other than the selected one, and are received by the signal amplifier module 3. In one example illustrated in FIG. 3, every one of the conductive wires 122 other than the leftmost one is electrically connected to the signal amplifier module 3. As shown in FIG. 5, a number of response signals (including response signals (A2) to (A5)), each having a waveform (for example, waveforms (S2) to (S5)), are received.

Afterwards, the signal amplifier module 3 amplifies the response signals received from the conductive wires 122 of the detection units 12 other than the selected one.

In step S105, the controller 4 receives amplified response signals from the signal amplifier module 3.

Afterwards, in step S106, the controller 4 controls the display 6 to display the amplified response signals received from the signal amplifier module 3.

Based on the amplified response signals displayed on the display 6, it may be determined whether the nerve 5 is injured.

Specifically, in step S107, the controller 4 is programmed to execute an algorithm to analyze the amplified response signals received from the signal amplifier module 3. Each of the response signals (and amplified response signals) has at least one crest (positive peak) and at least one trough (negative peak).

The algorithm includes, for each of the number of amplified response signals: first performing a pre-processing operation so as to move a baseline to a zero-point; afterwards, automatically setting a calculation window so as to obtain a waveform corresponding with the amplified response signal; then detecting a stimulus artifact in the waveform, and defining a first negative peak which is a first one that comes after the occurrence of the stimulus artifact; afterwards, determining a difference between a height of the first negative peak between adjacent one of the waveforms; and then, based on the difference of the heights, controlling the display 6 to display a specific color for the amplified response signal. For example, when the difference is smaller than a predetermined threshold, the specific color may be green to indicate the corresponding part of the nerve 5 is healthy. On the other hand, when the difference is larger than the predetermined threshold, the specific color may be red to indicate that the corresponding part of the nerve 5 is injured.

In the example as shown in FIG. 5, each of the waveforms (S2) to (S5) is defined as a physiologically complete waveform, and is substantially similar to one another. That is to say, the heights of the base trough are substantially equal for the waveforms (S2) to (S5). As a result, it may be determined that the corresponding parts of the nerve 5 attached to by the corresponding electrodes 121 are healthy.

In some embodiments, after the abovementioned steps, more detection may be performed in order to pinpoint which segment of the nerve 5 is injured.

For example, referring to FIGS. 3 and 5, the intraoperative nerve evaluation device 1 is placed to cover a front segment of the nerve 5, with the leftmost one of the electrodes 121 attached to the frontmost end of the nerve 5.

After the detection is done, the intraoperative nerve evaluation device 1 may be moved, and another one of the detection units 12 may be selected to provide the input signal to the nerve 5.

Figure 6:
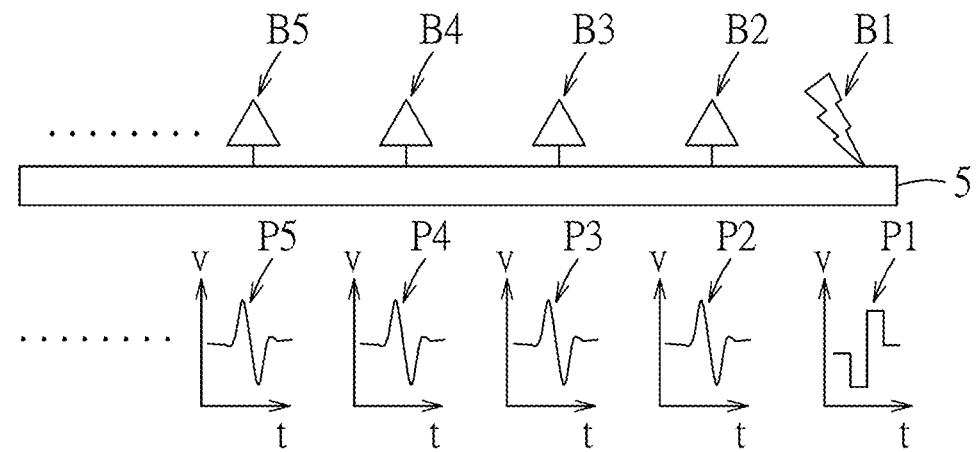
FIG. 6 illustrates the input signal being applied to another end of the healthy nerve and corresponding response signals.

FIGS. 3 and 6 illustrate the intraoperative nerve evaluation device 1 being placed to cover a rear segment of the nerve 5, and a rightmost one of the detection units 12 is selected and is attached to a rearmost end of the nerve 5. With the above setup, the steps S103 to S106 may be repeated. In use, an input signal (B1) having a waveform (P1) is applied to the rearmost end of the nerve 5, resulting in a number of response signals (including response signals (B2) to (B5)) having corresponding waveforms of (for example, waveforms (P2) to (P5)), respectively.

In the example as shown in FIG. 6, the waveforms (P2) to (P5) are each defined as a physiologically complete waveform, and are substantially similar to one another. That is to say, the heights of the first negative peaks are substantially equal for the waveforms (P2) to (P5). As a result, it may be determined that the corresponding parts of the nerve 5 attached to by the electrodes 121 are healthy.

Figure 7:
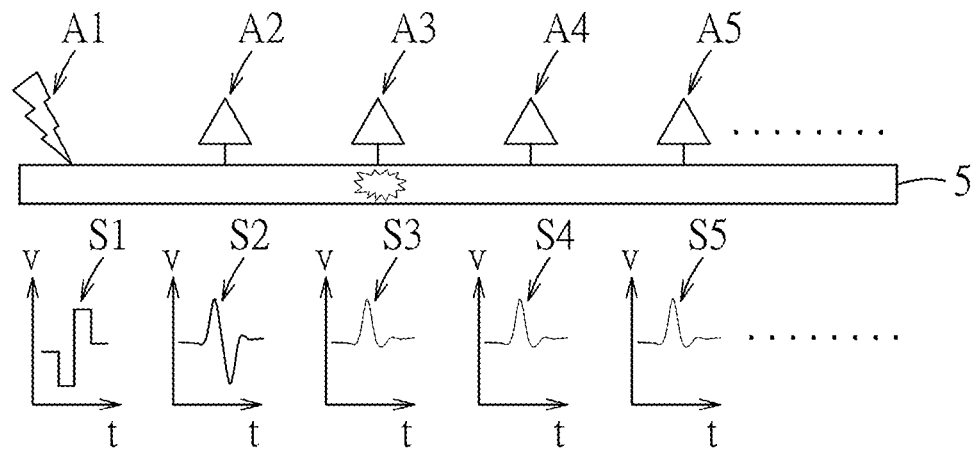
FIG. 7 illustrates the input signal being applied to one end of an injured nerve and corresponding response signals.
Figure 8:
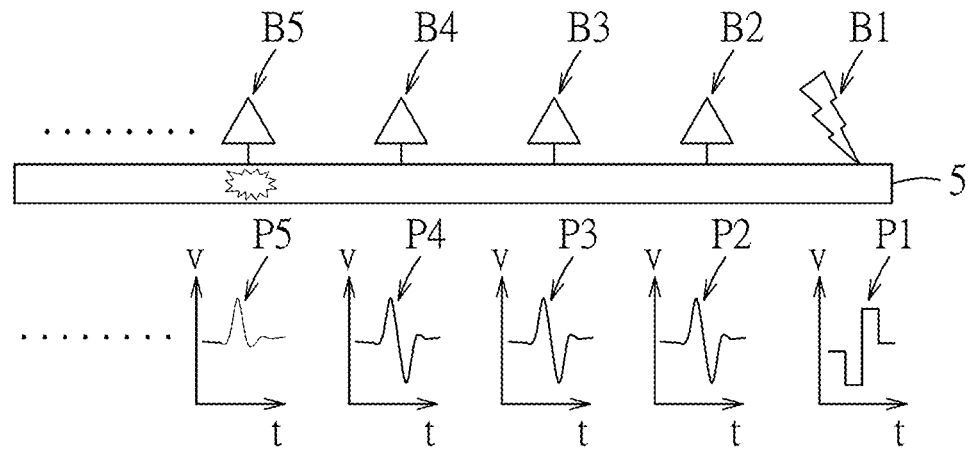
FIG. 8 illustrates the input signal being applied to another end of the injured nerve and corresponding response signals.

FIGS. 7 and 8 illustrate an injured nerve 5 being detected using the above method. The setup of the electrodes 121 in FIG. 7 is similar to that shown in FIG. 5.

In step S103, the leftmost one of the electrodes 121 applies the input signal (A1) to the frontmost end of the nerve 5. The resulting response signals (A2) to (A5) have different waveforms (S2) to (S5). It may be determined in step S106 that the waveforms (S3) to (S5) are not physiologically complete waveforms as defined above, and a height of the first negative peak of the waveform (S2) and a height of the first negative peak of the waveform (S3) have a difference therebetween that is larger than the predetermined threshold (that is to say, a difference of the first negative peaks obtained between adjacent detection units is larger than the predetermined threshold). That is to say, a difference of the first negative peaks obtained between adjacent detection units). As a result, the controller 4 may determine that a section of the nerve 5 after the point that is covered by the electrode 121 which receives the response signal (A3) is injured. That is, the response signal (A2) is displayed in green, and the response signals (A3) to (A5) are displayed in red.

Afterwards, as shown in FIG. 8, the electrodes 121 are moved to be attach to the rear segment of the nerve 5, with the rightmost one of the electrodes 121 attaching the rearmost end of the nerve 5. Then, steps S103 to S106 are repeated.

In step S103, the rightmost one of the electrodes 121 applies the input signal (B1) to the rearmost end of the nerve 5. The resulting response signals (B2) to (B5) have different waveforms (P2) to (P5). It may be determined in step S106 that the waveform (P5) is not a physiologically complete waveform as defined above, and a height of the first negative peak of the waveform (P4) and a height of the first negative peak of the waveform (P5) have a difference therebetween that is larger than the predetermined threshold. As a result, the controller 4 may determine that a section of the nerve 5 after the point that is covered by one of the electrodes 121 that receives the response signal (B5) is injured. That is, the response signals (B2) to (B4) are displayed in green, and the response signal (B5) is displayed in red.

Combining the detections as shown in FIGS. 7 and 8, it may be determined that a section of the nerve 5 between two parts (spots) where the response signals (A3) and (B5) are received is injured.

Figure 9:
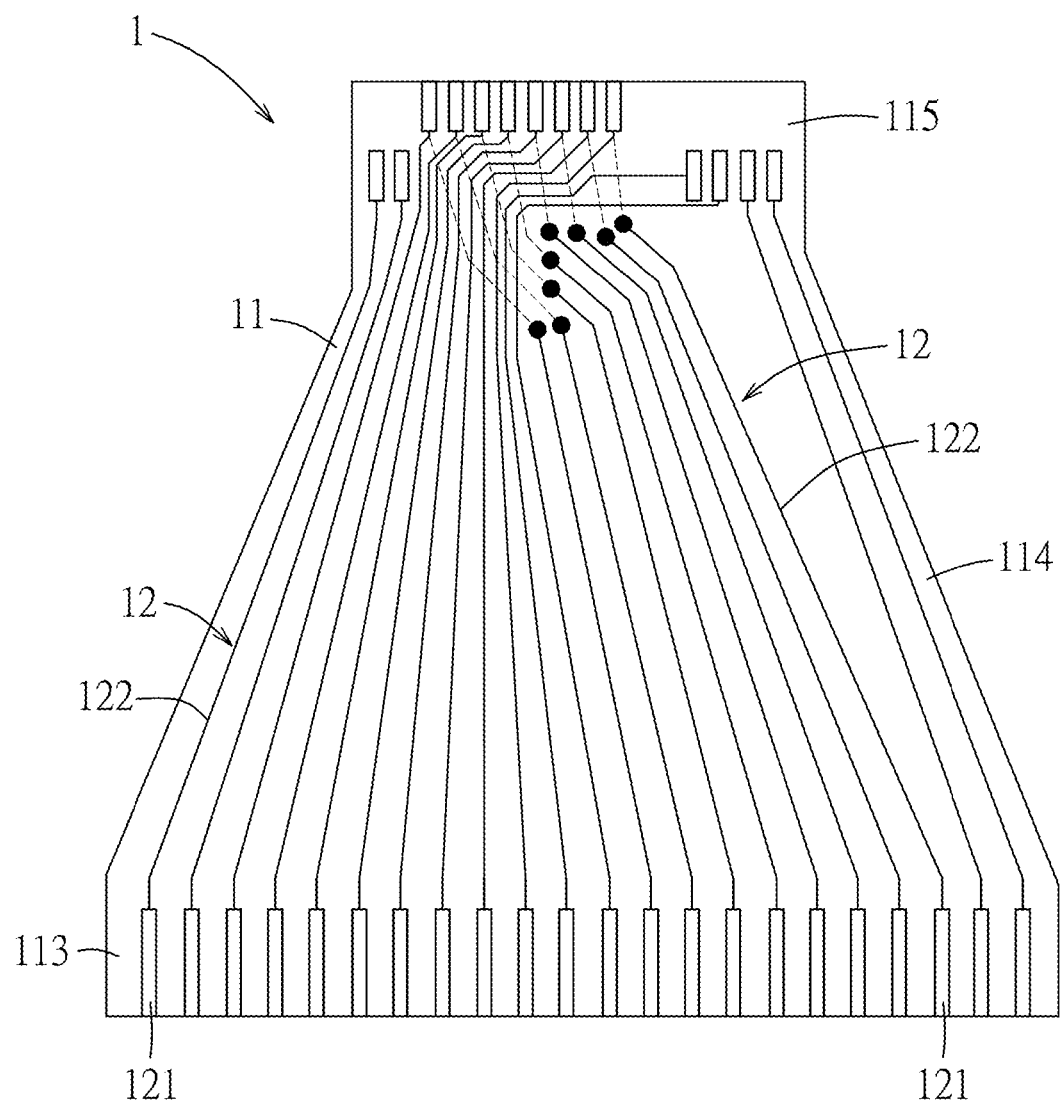
FIG. 9 is a schematic view of an intraoperative nerve evaluation device according to one embodiment of the disclosure.

FIG. 9 illustrates an intraoperative nerve evaluation device 1 according to one embodiment of the disclosure. In this embodiment, the shapes of the wire part 114 and the extension part 115 are modified in comparison with the embodiment depicted in FIGS. 1 and 2.

Figure 10:
FIG. 10 is a schematic view of an intraoperative nerve evaluation device according to one embodiment of the disclosure.

FIG. 10 illustrates an intraoperative nerve evaluation device 1 according to one embodiment of the disclosure. In this embodiment, each of the detecting units 12 is entirely arranged on the first surface 111 of the substrate 11, and the shape of the substrate 11 is rectangular without a tapering part.

Figure 11:
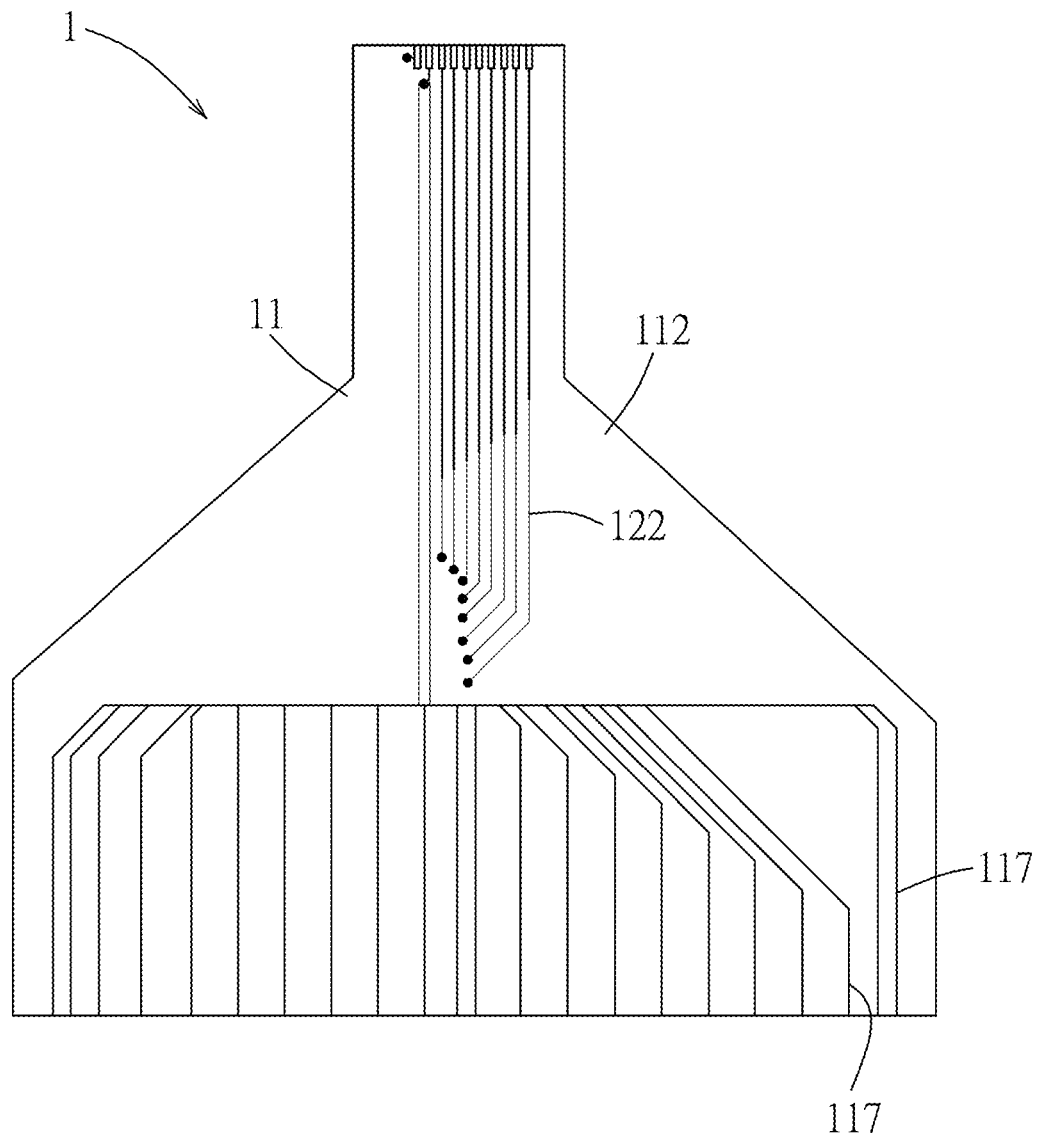
FIG. 11 is a schematic view of an intraoperative nerve evaluation device according to one embodiment of the disclosure.

FIG. 11 illustrates an intraoperative nerve evaluation device 1 according to one embodiment of the disclosure. In this embodiment, a number of conductive metal strips 117 are employed for the purpose of grounding. It is noted that since the conductive metal strips 117 do not entirely laminate on the second surface 112 of the substrate 11, this configuration may allow the substrate 11 to retain flexibility.

Figure 12:
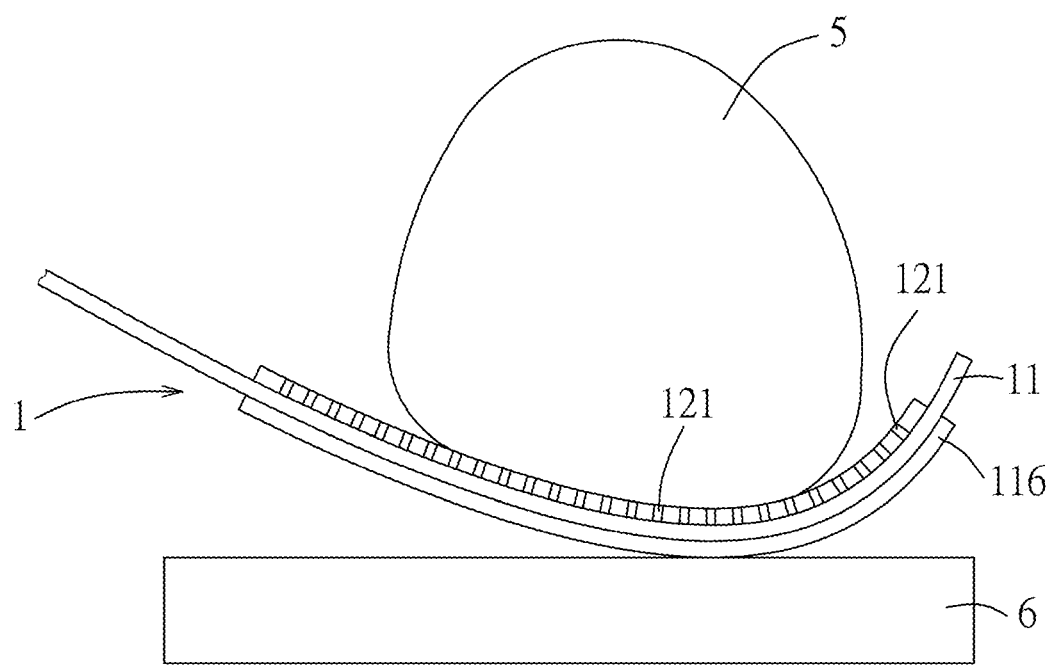
FIG. 12 is a schematic view of the intraoperative nerve evaluation device being attached to a nerve.

FIG. 12 illustrates the intraoperative nerve evaluation device 1 being attached to the nerve 5 as viewed from the side. It is noted that due to the flexibility of the substrate 11, the electrodes 121 may be fittingly attached to the nerve 5.

It is noted that the embodiments of the disclosure may be employed in various applications such as monitoring contractions of a muscle, performing an electromyography (EMG) operation, etc.

To sum up, the disclosure provides an intraoperative nerve evaluation device 1 including a number of electrodes 121 that are spaced apart from one another, and therefore may be able to monitor reactions of the nerve 5 in response to the input signal, and to efficiently determine which part, if any, of the nerve 5 is injured by attaching the intraoperative nerve evaluation device 1 to different parts of the nerve 5 and using different electrodes 121 to apply the input signal.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An intraoperative nerve evaluation system comprising:
   an intraoperative nerve evaluation device that includes a flexible substrate, and a plurality of detection units disposed on said substrate and spaced apart from one another, each of said detection units including an electrode and a conductive wire electrically connected to said electrode, said electrodes of said detection units being configured to be attached a nerve;
   a signal input module electrically connected to said conductive wire of a selected one of said detection units, and configured to transmit an input signal to said electrode of the selected one of said detection units;
   a controller electrically connected to said signal input module and configured to control operation of said signal input module;
   a signal amplifier module electrically connected to said controller and said conductive wires of said detection units other than the selected one, and configured to receive, from said conductive wires connected thereto, a number of response signals associated with the input signal, to amplify the response signals, and to transmit amplified response signals to said controller; and
   a display electrically connected to said controller and controlled by said controller to display the amplified response signals from said signal amplifier module;
   wherein the input signal transmitted by said signal input module is in the form of a bipolar stimulation signal, the response signals are generated from the nerve responding to the bipolar stimulation signal, each of the number of amplified response signals has at least one crest and at least one trough, and said controller is programmed to analyze each of the number of amplified response signals by:
      performing a pre-processing operation to so as to move a baseline of the amplified response signal to a zero-point;
      setting a calculation window so as to obtain a waveform corresponding with the amplified response signal;
      detecting a simulate artifact in the waveform, and defining a base negative peak which is a first negative peak that comes after the occurrence of the artifact;
      determining a difference of between a height of the base negative peak of the waveform and a height of the base trough of an adjacent one of the waveforms; and
      based on the difference of the heights, controlling said display to display the amplified response signal using an indicator to indicate a state of the part of the nerve corresponding with the amplified response signal.

2. The intraoperative nerve evaluation system of claim 1, wherein:
   said substrate has a first surface, and a second surface that is opposite to said first surface;
   said electrodes of said detection units are disposed on said first surface; and
   said conductive wires of some of said detection units are entirely arranged on said first surface, and said conductive wires of others of said detection units each extend on said first surface, pass through said substrate to said second surface and extend on said second surface.

3. The intraoperative nerve evaluation system of claim 2, wherein:
   said substrate has an electrode part, and a wire part extending and tapering from said electrode part in a first direction; and said electrodes of said detection units are disposed on said electrode part, and said conductive wires of said detection units extend from said electrode part to said wire part.

4. The intraoperative nerve evaluation system of claim 3, wherein said substrate further has an extension part that extends from one side of said wire part opposite to said electrode part in the first direction, and said conductive wires of said detection units further extend to said extension part.

5. The intraoperative nerve evaluation system of claim 4, wherein a width of said extension part in a second direction perpendicular to the first direction is smaller than that of said electrode part.

6. The intraoperative nerve evaluation system of claim 1, wherein:
said substrate has a first surface, and a second surface that is opposite to said first surface; and
each of said detection units is disposed on said first surface.

7. The intraoperative nerve evaluation system of claim 1, wherein said substrate is made of polyimide (PI).

8. A method for performing intraoperative nerve evaluation, the method to be implemented by a system that includes an intraoperative nerve evaluation device, a controller, a signal input module, a signal amplifier module and a display, the nerve evaluation device including a plurality of detection units that are disposed on a substrate and that are spaced apart from one another, each of the detection units including an electrode and a conductive wire coupled to the electrode, the electrodes of the detection units being attached to respective parts of a nerve of a subject, the signal input module being electrically connected to the conductive wire of a selected one of the detection units, the signal amplifier module being electrically connected to the conductive wire of each of the detection units other than the selected one, the method comprising:
a) controlling, by the controller, the signal input module to transmit an input signal to the electrode of the selected one of the detection units via the conductive wire of the selected one of the detection units;
b) receiving, by the signal amplifier module, a number of response signals from the conductive wires of the detection units other than the selected one;
c) amplifying, by the signal amplifier module, the number of response signals so as to generate a number of amplified response signals;
d) receiving, by the controller, the number of amplified response signals from the signal amplifier module; and
e) controlling, by the controller, the display to display the number of amplified response signals;

the method further comprising, after d):
f) analyzing, by the controller, the number of amplified response signals,
wherein the input signal transmitted by the signal input module is in the form of a bipolar stimulation signal, the response signals are generated from the nerve responding to the bipolar stimulation signal, each of the number of amplified response signals has at least one crest and at least one trough, and step f) includes, for each of the number of amplified response signals:
performing a pre-processing operation to so as to move a baseline of the amplified response signal to a zero-point;
setting a calculation window so as to obtain a waveform corresponding with the amplified response signal;
detecting a simulate artifact in the waveform, and defining a base negative peak which is a first negative peak that comes after the occurrence of the artifact
determining a difference of between a height of the base negative peak of the waveform and a height of the base trough of an adjacent one of the waveforms; and
based on the difference of the heights, controlling the display to display the amplified response signal using an indicator to indicate a state of the part of the nerve corresponding with the amplified response signal.

9. The method of claim 8, wherein the controller controls the display to display the amplified response signal in red when the difference is larger than a predetermined threshold, to indicate that the part of the nerve is in an injured state, and controls the display to display the amplified response signal in green when the difference is lower than the predetermined threshold to indicate that the part of the nerve is in a healthy state.

10. The method of claim 8, the electrode of the selected one of the detection units being attached to one of two end parts of the nerve, the method further comprising, after f):
repeating a) to f) with the signal input module being electrically connected to the conductive wire of another selected one of the detection units, the electrode of which is attached to the other one of the two end parts of the nerve, and with the signal amplifier module being electrically connected to the conductive wire of each of the detection units other than the selected one and the another selected one.

11. The method of claim 8, wherein the indicator is a specific color.

* * * * *